(12) United States Patent
Msika et al.

(10) Patent No.: US 8,304,453 B2
(45) Date of Patent: Nov. 6, 2012

(54) COMPOSITION COMPRISING AT LEAST ONE ALKANOLAMIDE TO INHIBIT MIGRATION OF LANGERHANS CELLS AND USES THEROF

(75) Inventors: Philippe Msika, Versailles (FR); Nathalie Piccardi, Saint Egreve (FR); Antoine Piccirilli, Versailles (FR)

(73) Assignee: Laboratoires Expanscience, Courbevoie (FR)

( * ) Notice: Subject to any disclaimer, the term of this patent is extended or adjusted under 35 U.S.C. 154(b) by 1439 days.

(21) Appl. No.: 11/411,870

(22) Filed: Apr. 27, 2006

(65) Prior Publication Data

US 2006/0194881 A1    Aug. 31, 2006

Related U.S. Application Data

(62) Division of application No. 10/499,977, filed on Jun. 24, 2004, now abandoned.

(30) Foreign Application Priority Data

Dec. 27, 2001 (FR) ...................... 01 16916

(51) Int. Cl.
*A01N 37/18* (2006.01)
*A01N 33/18* (2006.01)
*A01N 33/24* (2006.01)
*A61K 31/16* (2006.01)

(52) U.S. Cl. ...................... 514/625; 514/727
(58) Field of Classification Search ................. 514/625, 514/727
See application file for complete search history.

(56) References Cited

U.S. PATENT DOCUMENTS

| | | | |
|---|---|---|---|
| 6,001,375 A | 12/1999 | Lambers et al. | |
| 6,159,485 A | 12/2000 | Yu et al. | |
| 6,218,113 B1 | 4/2001 | Yue et al. | |
| 6,630,163 B1 * | 10/2003 | Murad ........................ 424/464 | |
| 6,846,812 B2 | 1/2005 | Dalko et al. | |
| 2003/0059447 A1 | 3/2003 | Lambers | |
| 2003/0215414 A1 | 11/2003 | Lambers | |
| 2004/0067910 A1 * | 4/2004 | Msika et al. .................. 514/78 |
| 2004/0101580 A1 | 5/2004 | Msika et al. | |
| 2004/0138177 A1 | 7/2004 | Park et al. | |

FOREIGN PATENT DOCUMENTS

| | | |
|---|---|---|
| DE | 19841794 A | 3/2000 |
| JP | 2000-186030 A | 7/2000 |
| WO | WO-88/04938 A1 | 7/1988 |
| WO | WO-95/29151 A | 11/1995 |
| WO | WO-98/21176 A1 | 5/1998 |
| WO | WO-99/29293 A | 6/1999 |
| WO | WO-99/41266 A | 8/1999 |
| WO | WO-02/072082 A | 9/2002 |

OTHER PUBLICATIONS

Sakai et al., Ceramide Derivatives as Therapeutic Agents, XP-001127407, Expert Opinion on Therapeutic Patents, vol. 8, No. 11, pp. 1673-1682 (1998).
Halliday et al., Protein Kinase C Transduces the Signal for Langerhans' Cell Migration From the Epidermis, XP-001011467, Immunology, vol. 79, pp. 621-626 (1993).
Arora et al., Stimulation In Vitro of Galactocerebroside Gallactosidase by N-Decanoyl 2-Amino-2-Methylpropanol, XP-000654675, Lipids, vol. 7, No. 1, pp. 56-59 (1972).
Newman, A Stereoselective Synthesis of D-Erythro-Spingosine, J. Am. Chem. Soc., vol. 95, No. 12; 4098-9, pp. 4098-4099 (Jun. 13, 1973).
Berardesca et al., Contact Dermatitis, vol. 45, No. 5, pp. 280-285 (2001).
Benjamins et al., "Effects of Ceramide Analogs on Myelinating Organ Cultures", Brain Research, vol. 102, 1976, pp. 267-281.

* cited by examiner

*Primary Examiner* — Yong Chong
(74) *Attorney, Agent, or Firm* — Birch, Stewart, Kolasch & Birch, LLP

(57) ABSTRACT

The invention concerns a composition containing at least an alkanolamide, optionally combined with at least a compound such as a metalloprotease inhibitor, a PKC inhibitor, an anti-inflammatory agent, a soothing agent, an immunosuppressor, an ion chelating agent, an oxazolin, an oxazolidinone and a carbamic acid derivative. The invention also concerns the use of such a composition as medicine, in particular its use for preventing or treating skin pathologies of allergic and/or inflammatory and/or irritative origin or resulting from a danger signal. The invention further concerns a method for cosmetic treatment of sensitive, irritated, intolerant, allergy-prone, ageing skin and/or mucosa exhibiting skin barrier disorder, or exhibiting non-pathological immunologic imbalance, which consists in applying such a composition on the skin and/or mucosa.

9 Claims, 2 Drawing Sheets

Figure 1:
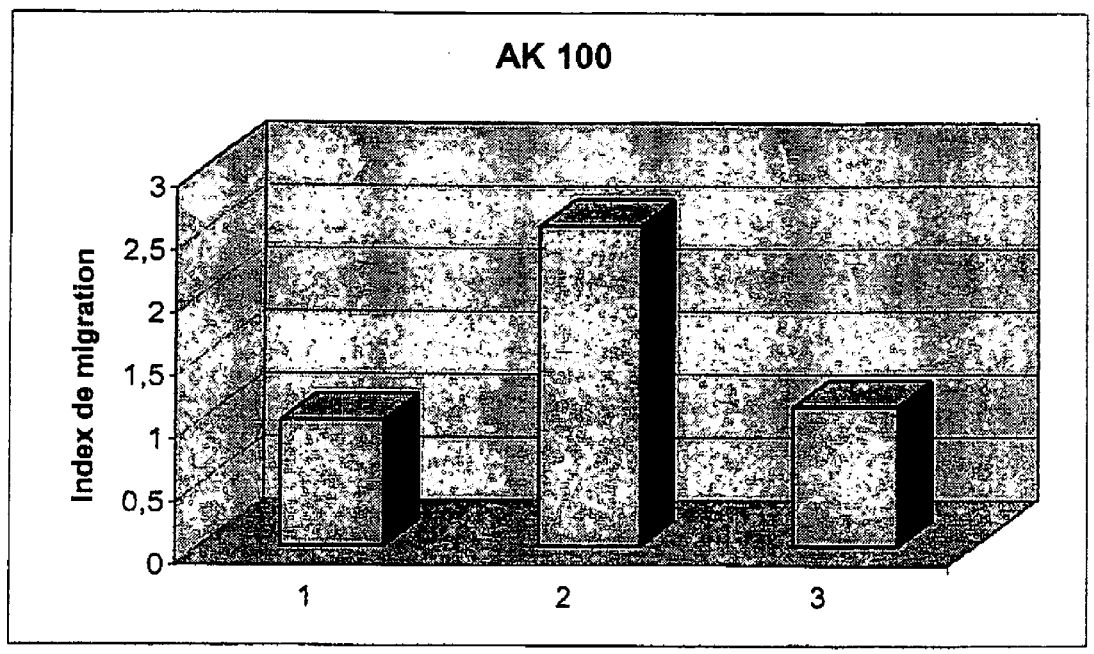

COMPOSITION COMPRISING AT LEAST ONE ALKANOLAMIDE TO INHIBIT MIGRATION OF LANGERHANS CELLS AND USES THEROF

This application is a Divisional of U.S. application Ser. No. 10/499,977 filed on Jun. 24, 2004 now abandoned, and for which priority is claimed under 35 U.S.C. §120; U.S. application Ser. No. 10/499,977 is the national stage application of International Application No. PCT/FR2002/004582 filed on Dec. 27, 2002; International Application No. PCT/FR2002/004582 claims the benefit of priority of Application No. 0116916 filed in France on Dec. 27, 2001 under 35 U.S.C. §119; the entire contents of all are hereby incorporated by reference.

This invention relates to the cosmetic and pharmaceutical treatment, and particularly dermatological treatment of the skin. More particularly, this invention relates to a composition containing at least one active compound chosen from among alkanolamides, possibly in combination with at least one other compound such as metalloprotease inhibitor, a PKC inhibitor, an anti-inflammatory agent, a soothing agent, an immunosuppressor, an ion chelating agent, an oxazolidinone, a derivative of carbamic acid or an oxazoline.

Another purpose of this invention is such a composition for use as a medicine, advantageously to inhibit migration of cells such as dermal dendrocytes, monocytes, lymphocytes and particularly Langerhans cells for example resulting from an external stimulus or "danger signal" with a chemical, physical, biological and more particularly immunity system origin, with a sufficiently high intensity to induce a disturbance of the cutaneous homeostasis. Alkanolamides and their combination with a metalloprotease inhibitor, a PKC inhibitor, an anti-inflammatory agent, a soothing agent, an immunosuppressor, an ion chelating agent, an oxazolidinone, a derivative of carbamic acid or an oxazoline and pharmaceutical compositions containing these products, are useful for the preparation of medicine for the treatment or prevention of skin pathologies with allergic and/or inflammatory and/or irritative and/or cutaneous discomfort origin (sensitive, reactive or intolerant skins).

Another purpose of the invention is a method for cosmetic treatment of sensitive, irritated, intolerant, allergy-prone, aging skin and/or mucosa, to which a danger signal is applied, exhibiting skin barrier disorder, with skin rashes or exhibiting non-pathological immunologic imbalance, consisting of applying such a composition on the skin and/or mucosa.

One of the main functions of the skin is to protect the organism against aggressions by the external environment. Much of this protection is provided by cooperation of cells present in the skin, that are capable of generating an inflammatory and/or immunity response directed against the noxious agent, in the presence of this noxious agent. These are dendritic cells, Langerhans cells (LC) of the epidermis, and dermal dendrocytes, monocytes, lymphocytes, keratinocytes, mastocytes and vascular endothelial cells.

LCs are dendritic cells derived from the bone marrow and that remain in non-lymphoid tissues such as the skin and mucosa (mouth, lung, bladder, rectum, vagina). In the skin, LCs are inserted between epidermal keratinocytes in the suprabasal position. Ultrastructurally, they are characterised by the presence of a specific organelle with membrane origin, namely the Birbeck granule. Immunohistochemically, LCs in particular express the CD1a molecule and class II Major Histocompatibility Complex molecules.

LCs play a determining role in immunity, as cells presenting the antigen. Experiments carried out in the mouse demonstrate that LCs capture antigens present in the epidermis and migrate to lymphoid tissues draining the skin, where they present the antigen to T cells. Initiation of the immune skin response depends on the capacity of LCs to leave the epidermis to migrate as far as the proximal ganglions. This migration can be influenced by different factors; the expression of adhesion molecules, proteins from the extracellular matrix, haptens, cytokines, etc. Nevertheless, the mechanisms involved in the migration of LCs are not yet completely elucidated. In particular, before reaching the lymphatic ganglions, LCs must firstly pass through the dermoepidermal junction (DEJ), but also they need to create a path through the dermal extracellular matrix (ECM). The DEJ is composed mainly of laminin 5, type IV and VII collagen, nidogen and perlecan. The ECM that surrounds fibroblasts in the dermis contains essentially type I and type III collagens.

Maturing, and the initiation and regulation of the migration of LCs depend on pro-inflammatory cytokines such as IL-1β (interleukin-1-beta) and TNF-α (Tumour Necrosis-alpha). The result is that any skin aggression, and particularly any inflammatory and/or irritative reaction capable of inducing a sufficient quantity of either or both of these cytokines, is capable of stimulating migration of LCs and therefore facilitating the allergic reaction if these LCs are associated with an antigen.

Dermatologic type pathologies may be observed as a result of the migration of LCs following the capture of a surface antigen. In atopic eczema, LCs are capable of fixing IgE on the surface and inducing a pathological immuno response. LCs play a central role in contact eczema, since they capture and treat the antigen before presenting it to T lymphocytes. The antigen will keep it in memory and the immuno reaction will be triggered on the second contact.

Considering the above, it is highly desirable to be able to modify the migrational capacity of dermal dendrocytes, monocytes, lymphocytes, Langerhans cells (LCs), to attempt to increase the tolerance threshold or to limit the reactivity of the allergic and/or inflammatory and/or irritated skin and the atopic and/or sensitive and/or reactive and/or uncomfortable skin. This is the problem that this invention is intended to solve. The inventors have demonstrated that quite surprisingly and unexpectedly, compounds such as alkanolamides are capable of spectacularly inhibiting the migration of cells such as Langerhans cells, induced particularly by the presence of an allergen agent. However, in the past alkanolamides have never been described as being capable of inhibiting the migration of Langerhans cells induced particularly by the presence of an allergen agent.

This invention thus relates to a composition comprising at least one active compound for inhibiting the migration of Langerhans cells chosen from among the alkanolamides group. Advantageously the composition according to the invention is a cosmetic or pharmaceutical composition, and particularly a dermatological composition, comprising at least one cosmetically and pharmaceutically acceptable excipient.

Alkanolamides according to the invention satisfy the following general formulas:

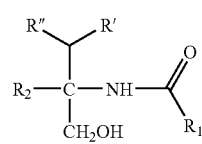

in which $R_1$ represents an alkyl group in $C_1$-$C_{40}$ comprising 0 to 6 unsaturations and possibly comprising at least one substitute chosen from the group formed by hydroxyl radicals (OH), alkoxy radicals in $C_1$-$C_6$ ($OC_1$-$C_6$) and carbonyl alkoxy radicals in $C_1$-$C_6$ ($COOC_1$-$C_6$);

R' and R" independently represent a hydrogen atom, a methyl group, a hydroxyl group, an alkyl group in $C_2$-$C_{20}$ comprising 0 to 6 unsaturations and possibly comprising at least one substitute chosen from the group formed by hydroxyl radicals (OH) and alkoxy radicals in $C_1$-$C_6$ ($OC_1$-$C_6$), provided that when R' represents a hydroxyl group, R" represents a hydrogen or an alkyl group in $C_1$-$C_6$ comprising from 0 to 3 unsaturations and possibly at least one substitute chosen from the group formed by hydroxyl radicals (OH), alkoxy radicals in $C_1$-$C_6$ ($OC_1$-$C_6$) and carbonyl alkoxy radicals in $C_1$-$C_6$ ($COOC_1$-$C_6$).

$R_2$ represents a hydrogen atom, a methyl group, an alkyl group in $C_2$-$C_{20}$ comprising 0 to 6 unsaturations and possibly at least one substitute chosen from the group formed by hydroxyl radicals (OH), alkoxy radicals in $C_1$-$C_6$ ($OC_1$-$C_6$) and carbonyl alkoxy radicals in $C_1$-$C_6$ ($COOC_1$-$C_6$).

For the purposes of this invention, the term "alkoxy radical in $C_1$-$C_6$ ($OC_1$-$C_6$)" means an alkoxy radical in which the alkyl group comprises between 1 and 6 carbon atoms.

Advantageously, the radical $R_1$ represents a saturated linear alkyl group comprising 2 to 40 carbon atoms (in $C_2$-$C_{40}$), advantageously 6 to 22 carbon atoms (in $C_6$-$C_{22}$), and even more advantageously from 8 to 18 carbon atoms (in $C_8$-$C_{18}$), and even more advantageously from 10 to 16 carbon atoms (in $C_{10}$-$C_{16}$).

In another embodiment of the invention, the radical $R_1$ represents an alkyl group comprising 1 to, 40 carbon atoms (in $C_1$-$C_{40}$) advantageously 2 to 40 carbon atoms (in $C_2$-$C_{40}$), preferably 6 to 22 carbon atoms (in $C_6$-$C_{22}$) and even more advantageously from 8 to 18 carbon atoms (in $C_8$-$C_{18}$), comprising 1 to 6 unsaturations and possibly including at least one hydroxyl, alkoxy, or carbonyl alkoxy radical as defined above.

According to one embodiment of the invention, R' and R" independently represent a hydrogen atom, a methyl group, a linear alkyl group saturated in $C_2$-$C_{20}$.

According to another embodiment of the invention, $R_2$ represents a hydrogen atom, a methyl group or a linear alkyl group saturated in $C_2$-$C_{20}$.

Advantageously, according to this invention, the radical $R_1$ represents a linear alkyl group saturated in $C_2$-$C_{40}$, advantageously in $C_6$-$C_{22}$, and even better in $C_8$-$C_{18}$, and even better still in $C_{10}$-$C_{16}$, and R' and R" independently represent a hydrogen atom, a methyl group or a linear alkyl group saturated in $C_2$-$C_{20}$, and $R_2$ represents a hydrogen atom, a methyl group or a linear alkyl group saturated in $C_2$-$C_{20}$.

According to one advantageous embodiment of the invention, the said alkanolamide is the alkanolamide called AK100 with the following formula:

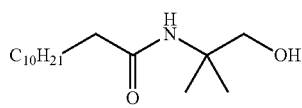

One particular process for the preparation of alkanomides comprising a carbonyl alkoxy group in $C_4$-$C_{40}$ is described in European patent application EP 968 998.

According to one embodiment of the invention, the composition may also comprise at least one inhibitor of the migration of Langerhans cells selected in the group of matrix metalloprotease (MMP) inhibitors.

For the purposes of this invention, "matrix metalloprotease (MMP) inhibitor compounds" refers to any compound known to those skilled in the art for its capability of inhibiting the degradation activity of the extracellular matrix by MMPs. MMPs form a family of zinc-dependent enzymes (more than twenty have been identified and characterised) with a very preserved structure, that have the capacity of degrading components of the extracellular matrix. Depending on the nature of their substrate, they are classified into collagenases, gelatinases and stromelysin. They may be synthesised by different cellular types in the skin (fibroblasts, keratinocytes, macrophages, endothelial cells, eosinophilic cells, Langerhans cells, etc.). The group of MMPs is thus composed of four subclasses, namely (1) collagenases, (2) gelatinases, (3) stromelysins and (4) membrane-type MMPs (MT-MMPs). The activity of MMPs may be modulated by naturally present proteinase inhibitors such as tissue inhibitors of metalloproteinases (TIMPs, and particularly TIMP-1 and TIMP-2). In particular, the active compound for inhibiting migration of Langerhans cells is a compound inhibiting at least one MMP chosen from among the group composed of MMP-1, MMP-2, MMP3 MMP-9, MMP-7, MMP-13 and MMP-18. For the purposes of this invention, "MMP inhibiting compound" means an active compound that inhibits the migration of Langerhans cells, particularly tissue inhibitors of metalloproteinases (TIMPs), alpha-2-macroglobuline, plasminogen activator inhibitors, zinc chelating agents, bryostatine-1, antibiotics (doxycyclines, minocylines, etc.), synthetic or natural peptides with a structure similar to the structure of substrates of MMPs (batimastat, marimastat, etc.), retinoids (particularly non aromatic retinoids such as retinaldehyde, tretinoin and retinoic acid 9-cis, vitamin A, monoaromatic retinoids such as etretinate, all-trans acitretine and motrerinide, polyaromatic retinoids such as adapalene, tazarotene, tamibarotene and sulfone methyl arotinoid), and antioxidants (singlet oxygen traps, etc.), anti-cancer agents (or "anti-metastatic" agents), malt hydrolysates such as Colalift marketed by the Coletica Company, extracts of marine algae such as Kelpadelie marketed by the Secma Company, shark cartilage extracts such as the MDI complex marketed by the Atrium Company, rice peptides such as Colhibin marketed by the Pentapharm Company, peptide extracts of lupin. More particularly, the MMP inhibiting compound according to this invention is chosen from the group composed of peptide extracts of lupin or "lupin peptides" as described in patent application FR 99 04 875 deposited on Apr. 19 1999 on behalf of the Laboratoires Pharmascience Company. In particular, we would like to mention the peptide extract described in application FR 99 04 875 under the name extract B (LU105). According to another preferred embodiment of the invention, the said MMP inhibitor is chosen from the group composed of retinoids.

According to one particular embodiment of the invention, the composition may also include at least one compound chosen from the group composed of PKC inhibitors, anti-inflammatory agents, soothing agents, immunosuppressors, ion chelating agents, oxazolidinones, derivatives of carbamic acid, particularly (1-Hydroxymethyl-tridecyl)-carbamic acid and (1-Hydroxymethyl-undecyl)-carbamic acid and alkanolamides. This or these compound(s) chosen from the group composed of PKC inhibitors, anti-inflammatory agents, soothing agents, immunosuppressors, ion chelating agents, oxazolidinones, derivatives of carbamic acid, particularly (1-Hydroxymethyl-tridecyl)-carbamic acid and (1-Hydroxymethyl-undecyl)-carbamic acid and alkanolamides make it possible to modify and/or limit the irritative or sensitisation reaction, and for some of them also even to inhibit migration of dendritic cells, more particularly Langerhans cells, dermal dendrocytes, monocytes, lymphocytes, keratinocytes, mastocytes and endothelial cells.

For the purpose of this invention, "PKC" or "Protein Kinase C" means enzymes that catalyse a phosphorylation reaction on a cell substrate.

When they are activated, PKCs phosphorylate specific serine or threonine residues on protein substrates, that vary depending on the cell type. In many cells, activation of PKCs increases the transcription of specific genes.

Protein Kinase C (PKC) denotes a protein coded by a family of genes (11 different isoforms). In particular, it is known that these proteins are involved in transduction of extracellular signals mediated by growth factors, cytokines, and a number of other biological molecules. Protein Kinase β2 (PKC-β2) appears specifically expressed by LCs of the epidermis.

Thus, any compound known to those skilled in the art as inhibiting the phosphorylation activity of PKCs can be used as a PKC inhibiting compound according to this invention. For example, consider the example of polypeptides described in application WO 99 43805 (Incyte Genomics Inc.).

In particular, the PKC inhibiting compound is chosen from the group composed of non-specific PKC inhibitors, specific inhibitors of isoform PCK-β2 and associations of these compounds.

More particularly, the PKC inhibiting compound is chosen from the group composed of phenolic and polyphenolic compounds, procyanidins (catechines, epicatechines, etc.) alpha-amyrine, lupeol, linoleate lupeol, sterols, stanols, triterpenic alcohols and their hydrogenated homologues, antibiotics such as staurosporine, Ro-318425 (or 2-(8)-(aminomethyl)-6,7,8,9-tetrahydropyridol (1,2-a)indol-3-yl)3-(1-methyl-indol-ylmaleimide, HCl) as marketed by the Calbiochem Company, compounds that act by competition with physiological activators of PKCs such as diacylglycerol and phorbol ester, cutaneous lipids of the (lyso)sphingolipid, lysophospholipid types such as ceramides and pseudoceramides, sphingosines and phytosphingosines, sphinganines, and derivatives, precursors, analogues and homologues of these compounds, with natural or synthetic origin.

For the purposes of this invention, "phenolic and polyphenolic compounds" means simple phenols, benzoquinones, phenolic acids, acetophenones, phenylacetic acids, hydroxycinnamic acids, coumarins and isocoumarins, chromones, naftoquinones, xanthones, anthraquinones, flavonoids, lignanes and neolignanes, lignines, chalcones, dihydrochalcones, aurones, flavones, flavonols, dihydroflavonols, flavanones, flavanols, flavandiols or leucoanthocyanidins, anthocyanidins, isoflavonoids, biflavonoids, proanthocyanidins and condensed tannins.

For the purposes of the invention, "sterols" means specifically sterol, in other words the perhydro-1,2-cyclopentanophenanthrene compound with a hydroxyl group in position 3, and analogues of sterol with the general formula (1) given below.

Thus, preferably, sterols that can be used according to the invention preferably satisfy the general formula given below:

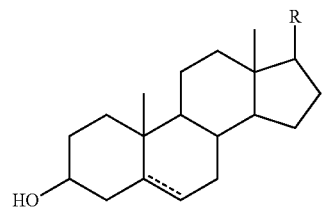

(I)

in which the unsaturation shown in dashed lines in position 5 corresponds to unsaturation in the case of sterols, R represents a hydrocarbonated chain, linear or ramified, unsaturated or not unsaturated, comprising 1 to 25 carbon atoms. In particular, R is chosen from the group composed of alkyl groups in $C_1$-$C_{12}$, alkoxy groups in $C_1$-$C_8$, alkenyl groups in $C_2$-$C_8$, alkynyl groups in $C_2$-$C_8$, halogenated alkenyl groups in $C_2$-$C_8$, halogenated alkynyl groups in $C_2$-$C_8$. The term "halogenated" denotes one or several halogen substitutes, namely one or several atom(s) of chlorine, fluorine, bromine or iodine.

Sterols that can advantageously be used according to the invention include particularly β-sitosterol, α-sitosterol, γ-sitosterol, stigmasterol, campesterol or brassicasterol and mixes of these compounds. For example, β-sitosterol can be used in the form of a product named "Ultra" (comprising mainly β-sitosterol) as marketed by the Kaukas Company. Examples of mixes of sterols include the product called "Generol" comprising mainly β-sitosterol (about 50% by weight), stigmasterol, brassicasterol or campesterol as marketed by the Cognis Company, and the "Primal" product made by the Kaukas Company.

Triterpenic alcohols that can advantageously be used according to the invention include in particular β-amyrine, erythrodiol, taraxasterol, cycloartenol, 24-methylenecycloartanol, lupeol, lanosterol and mixes of these compounds.

For the purposes of this invention, "hydrogenated homologues" of a triterpenic alcohol means corresponding triterpenic alcohol compound(s) for which any unsaturated bond(s) that is (are) present have been hydrogenated (in other words transformed into a saturated bond) using methods well known to those skilled in the art.

More particularly, the PKC inhibiting compound is chosen from the group composed of sphingolipids and lysophospholipids such as:
  ceramics
  sphingosines
  galactocerobrosides
  psychosines
  sulfatides
  lysosulfatides
  sphyngomyelins, and
  lysosphingomyelins.

Note also that cutaneous lipids of the sphingolipid and lysophospholipid types can be used in particular as a PKC inhibiting compound.

Some of the most elementary sphingolipids that can be used are sphingosine (D erythro dihydroxy 1,3 amino 2 octadecene 4t) and its isomers, and phytosphingosine (D ribo trihydroxy 1,3,4 amino 2 octadecane) and its isomers. But lysosphingolipids (including lysosulfatide and psychosine), solfogalactosylsphingosine, sphinganine (2-amino 1,3 octadecane diol) and sphingomyelins can also be used.

Phospholipids in the phosphatidylamino-alcohol and phosphatidylpolyol families can be used. The phosphatidylamino-alcohols group includes particularly phosphatidylethanolamines (or phosphatidylcolamines), phosphatidylcholines, phosphatidylserines, N-acylphosphatidylethanolamines. The phosphatidylpholyols group includes phosphatidylcholinositols, diphosphoinositides, lysodiphospho-inositides, phosphatidylglycerols and cardiolipids.

Note also more particularly that PKC inhibiting compounds used may include ceramides, particularly ceramides of the intercorneocyte cement of the epidermis and ceramide precursors, namely sphingosine and phytosphingosine.

In general, ceramides may be synthesised chemically (they are frequently called pseudo-ceramides), or they may be of animal origin (relatively high concentrations of sphingolipids are present in the encephalus and the spinal cord of mammals) or plant origin (namely cerebrosides and another glycosylated sphongolipids) or derivates of yeasts (stereochemical configuration identical to that of ceramides naturally present in the human skin).

Ceramides of the intercorneocyte cement of the epidermis may be separated by conventional methods (thin layer chromatography) into six fractions corresponding to compounds that differ by the nature of fatty acids and the nature of the base involved (sphingosines, unsaturated, or phytosphingosines, saturated). The following table 1 illustrates the corresponding structures in these fractions, according to the Werts and Downing classification. Fraction 6 itself may be sub-divided by finer methods into two entities, ceramides 6a and 6b.

TABLE 1 the six main fractions of ceramides in the epidermis

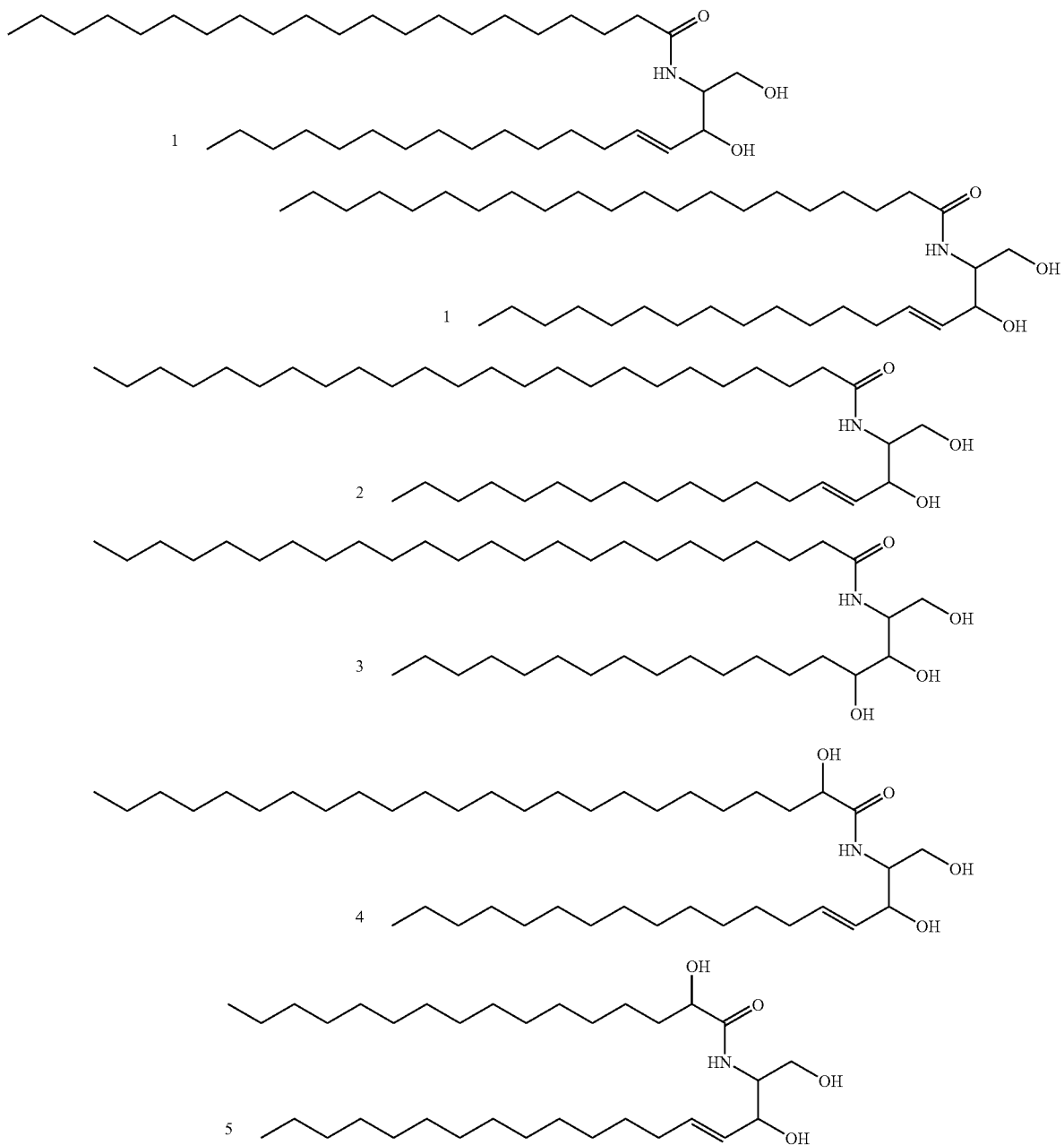

TABLE 1-continued the six main fractions of ceramides in the epidermis

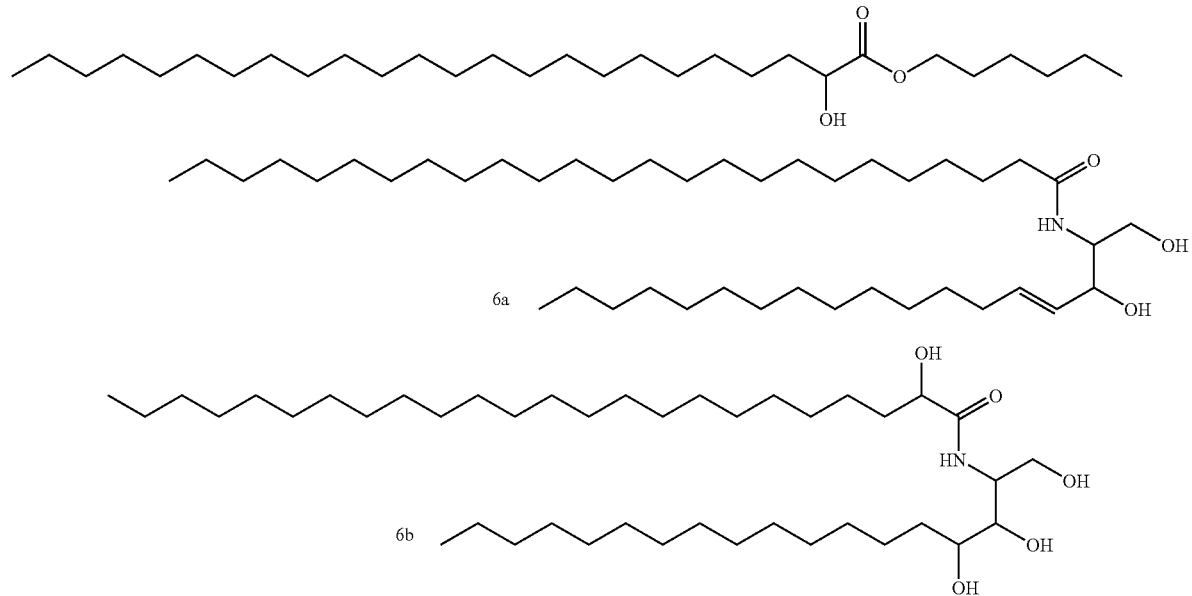

Thus, ceramides 1, the least polar, comprise a very special structure that is repeated in ceramide 6a: an omega-hydroxyacid with a long chain amidifying the base, and attached at its omega end by an ester bond to another fatty acid (0-acylceramides). In the case of fraction 1, fatty acids bonded to sphingosine are essentially in C24, C26, C30, C32 and C34 and they may be saturated, monoethylenic (mainly for C30, C32 and C34) or diethylenic (C32 and especially C34). The fatty acid attached to the omega end of the previous item, it is predominantly linoleic acid for ceramides 1, the essential role of the epidermis hybrid barrier function is well known.

Fraction 2 has a more classical structure (sphingosines or dihydrosphingosines bonded by an amide bond to a fatty acid, mainly $C_{20}$ to $C_{28}$) is the most frequent.

Fraction 3 is fairly similar, the only difference applying to the nature of the base, which in this case is represented essentially by saturated phytosphingosines.

Fractions 4 and 5 are characterised essentially by the presence of alpha-hydroxyacids bonded to a sphingosine.

Fraction 6b is similar to fractions 4 and 5, comprising an alpha hydroxyacid, but bonded to a saturated phytosphingosine.

Fraction 6a, like the ceramide 1, comprises the characteristic pattern that is only located in ceramides in the epidermis, in other words the ester bond between the omega hydroxyl of a fatty acid bonded to a sphingosine, and the carboxylic group of a terminal fatty acid which in this case is an alpha-hydroxyacid rather than linoleic acid.

Note also phytoceramides (ceramides based on phytosphingosin), synthetic cholesterol-ceramides, galacto or gluco cerebrosides.

Finally, the PKC inhibiting compounds that may be used according to this invention include sphingosine that is present in the natural state in the skin, and also plays an important role in the barrier function of the stratum corneum, as a precursor of sphingolipids (ceramides and sphingoglycolipids). It may be derived from a biological source such as cattle brain extracts or by a synthetic method starting from serine for example as described in the article by Newman, J. Am. CHEM., 95 (12): 4098 (1973). More particularly, note the isomer forms of sphingosine, D-erythro, L-threo, L-erythro and D-threo. The D-erythro form is the form most frequently present in nature.

According to this invention, PKC inhibiting compounds that can be used include isomers, derivatives (salts, complexes, etc.), analogues, homologues, precursors and metabolites of the PKC inhibiting compounds described above.

The anti-inflammatory agents that can be used in the context of this invention in association with oxazolines are Non Steroidal Anti-Inflammatory Drugs (NSAID).

The soothing agents that can be used in the context of this invention in combination with oxazolines are advantageously derivatives of liquorice and derivatives of alpha-bisabolol.

The immunosuppressors that can be used in the context of this invention in association with oxazolines are advantageously tacrolimus, pimecrolimus, and cyclosporine.

The ion chelating agents that can be used in the context of this invention in association with oxazolines are advantageously chemical chelating agents advantageously chosen from the group composed of ethylenediamine-tetraacetic acid (EDTA) and salts of sodium, potassium, calcium disodium, diammonium, triethanololamine (TEA-EDTA), hydroxyethyl ethylene diamine tetraacetic acid (HEDTA) and its trisodium salt, diethylenetriamine pentacetic acid (DTPA) and mixes of them. The ion chelating agents may also be biological chelating agents advantageously chosen from the group composed of metallothionein, transferrin, lactoferrin, calmoduline, chitosane methylene phosphonate and mixes of them.

The chelated ions are advantageously the $Na^+$, $K^+$, $Ca^{2+}$, $Cl^-$, $Ni^{2+}$, $Co^+$, $Co^{2+}$, $Zr^{2+}$, $Zr^{4+}$ ions, but also chromium ions at oxidation level II and III such as $Cr^{2+}$, $Cr^{3+}$ and $Cr_2O_7^{2-}$.

The oxazolines that can be used in the context of this invention in association with alkanolamides are advantageously oxazolines satisfying the following general formulas:

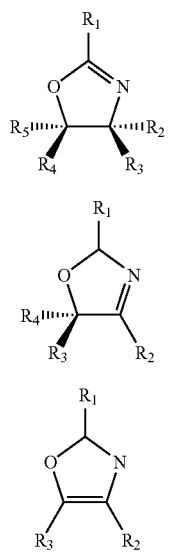

in which $R_1$ represents an alkyl group in $C_1$-$C_{40}$, linear or ramified, saturated or unsaturated and possibly including one or several ethylenic unsaturation(s), and one or several substitute(s) chosen from the group formed by hydroxy (OH) and alkoxy radicals in $C_1$-$C_6$ ($OC_1$-$C_6$), and $R_2$, $R_3$, $R_4$ and $R_5$ independently represent a hydrogen atom, a hydroxy radical, or an alkyl group in $C_1$-$C_{30}$, linear or ramified, saturated or unsaturated, possibly including one or several ethylenic unsaturation(s), and one or several substitute(s) chosen from among the group formed by the hydroxy radical (OH), alkoxy in $C_1$-$C_6$ ($OC_1$-$C_6$) radicals and carbonyl alkoxy radicals in $C_1$-$C_6$ ($COOC_1$-$C_6$). For the purposes of this invention, the term "alkoxy in $C_1$-$C_6$ ($OC_1$-$C_6$)" means an alkoxy radical in which the alkyl group comprises 1 to 6 carbon atoms.

Advantageously according to this invention, the said oxazoline is a type 1 oxazoline selected from the group composed of 2-undecyl-4-hydroxymethyl-4-methyl-1,3-oxazoline, 2-undecyl-4,4-dimethyl-1,3-oxazoline, (E)-4-, 4-dimethyl-2-heptadec-8-enyl-1,3-oxazoline, 4-hydroxymethyl-4-methyl-2-heptadecyl-1,3-oxazoline, (E)-4-hydroxymethyl-1-4-methyl-2-heptadec-8-enyl-1,3-oxazoline, and 2-undecyl-4-ethyl-4-hydroxymethyl-1,3-oxazoline. Preferably, the said oxazoline is 2-undecyl-4,4-dimethyl-1,3-oxazoline called OX-100 and its formula is:

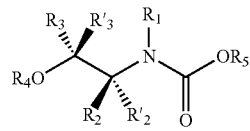

The derivatives of carbamic acid that can be used within the context of this invention in association with alkanolamides are advantageously derivatives of carbamic acid satisfying the following general formula:

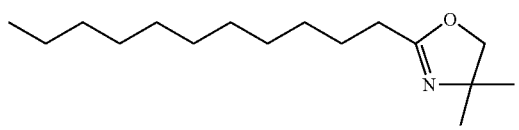

in which:

$R_1$ represents a hydrogen atom or an alkyl group in $C_1$-$C_{30}$, linear or ramified, saturated or unsaturated, possibly including one or several ethylenic and/or acetylenic unsaturations, and one or several hydroxy substitutes (OH);

$R_2$ and $R'_2$ independently represent a hydrogen atom or an alkyl group in $C_1$-$C_{30}$, linear or ramified, saturated or unsaturated, possibly including one or several ethylenic and/or acetylenic unsaturations, and one or several hydroxy substitutes (OH);

$R_3$ and $R'_3$ independently represent a hydrogen atom or an alkyl group in $C_1$-$C_{30}$, linear or ramified, saturated or unsaturated, possibly including one or several ethylenic and/or acetylenic unsaturations, and one or several hydroxy substitutes (OH);

$R_4$ and $R_5$ independently represent a hydrogen atom or an acyl group of the RxCO type in which Rx is an alkyl radical in $C_1$-$C_{30}$, linear or ramified, saturated or unsaturated, possibly including one or several ethylenic and/or acetylenic unsaturations, and one or several hydroxy substitutes (OH);

According to one embodiment, $R_1$ represents a hydrogen atom.

According to another embodiment, $R_2$ represents a linear alkyl group saturated in $C_8$-$C_{22}$, advantageously in $C_9$-$C_{18}$, even more advantageously in $C_9$-$C_{13}$, and even more advantageously in $C_{11}$-$C_{13}$ and/or $R'_2$ represents a hydrogen atom.

According to another embodiment, $R_3$ and $R'_3$ represent a hydrogen atom.

According to another embodiment, $R_4$ and $R_5$ represent a hydrogen atom.

In one particular embodiment, $R_1$ represents a hydrogen atom, $R_2$ represents a linear alkyl group saturated in $C_8$-$C_{22}$, advantageously in $C_9$-$C_{18}$, even more advantageously in $C_9$-$C_{13}$ and even more advantageously in $C_{11}$-$C_{13}$, and $R'_2$, $R_3$, $R'_3$, $R_4$ and $R_5$ represent a hydrogen atom.

Advantageously, the derivative of carbamic acid is chosen from the group composed of (1-Hydroxymethyl-tridecyl)-carbamic acid and (1-Hydroxymethyl-undecyl)-carbamic acid.

(1-Hydroxymethyl-tridecyl)-carbamic acid can be represented by the following formula:

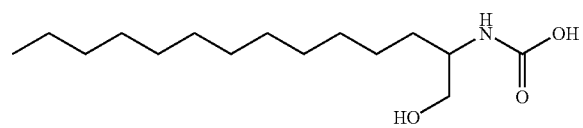

Oxazolidinones that can be used within the context of this invention in association with alkanolamides are advantageously oxazolidinones satisfying the following general formula:

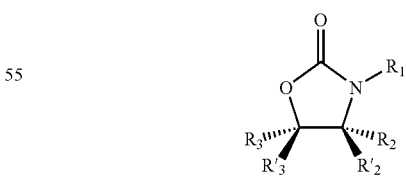

in which:

$R_1$ represents a hydrogen atom or an alkyl group in $C_1$-$C_{30}$, linear or ramified, saturated or unsaturated, possibly comprising one or several ethylenic and/or acetylenic unsaturations, and one or several hydroxy substitutes (OH);

$R_2$ and $R'_2$ independently represent a hydrogen atom or an alkyl group in $C_1$-$C_{30}$, linear or ramified, saturated or unsaturated, possibly including one or several ethylenic and/or acetylenic unsaturations, and one or several hydroxy substituents (OH);

$R_3$ and $R'_3$ independently represent a hydrogen atom or an alkyl group in $C_1$-$C_{30}$, linear or ramified, saturated or unsaturated, possibly including one or several ethylenic and/or acetylenic unsaturations, and one or several hydroxy substituents (OH);

According to one embodiment, $R_1$ represents a hydrogen atom.

According to another embodiment, $R_2$ represents a linear alkyl group saturated in $C_8$-$C_{22}$, advantageously in $C_9$-$C_{18}$, even more advantageously in $C_9$-$C_{12}$ and even more advantageously in $C_{10}$-$C_{11}$, and/or $R'_2$ represents a hydrogen atom.

According to another embodiment, $R_3$ and $R'_3$ represent a hydrogen atom.

In one particular embodiment, $R_1$ represents a hydrogen atom, $R_2$ represents a linear alkyl group saturated in $C_8$-$C_{22}$, advantageously in $C_9$-$C_{18}$, even more advantageously in $C_9$-$C_{12}$ and even more advantageously in $C_{10}$-$C_{11}$, and $R'_2$, $R_3$ and $R'_3$ represent a hydrogen atom.

Advantageously, the oxazolidinone is chosen from the group composed of 4-dodecyl-oxazolidin-2-one, 3,4-didodecyl-oxazolidin-2-one and 4,5-didodecyl-oxazolidin-2-one.

4-dodecyl-oxazolidin-2-one can be represented by the following formula:

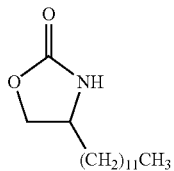

3,4-didocyl-oxazolidin-2-one may be represented by the following formula:

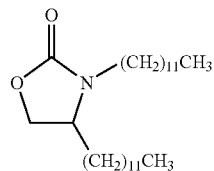

4,5-didodecyl-oxazolidin-2-one may be represented by the following formula:

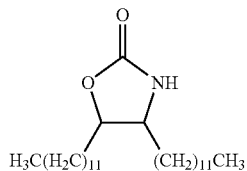

Oxazolines, oxazolidinones and derivatives of carbamic acid are compounds inhibiting the migration of Langerhans cells.

The composition according to the invention is characterised in that the concentration of alkanolamide is advantageously between about 0.001 and about 10% by weight, and more particularly between 0.01 and 3% by weight, compared with the total weight of the composition.

The composition according to this invention is advantageously a cosmetic or pharmaceutical composition, and particularly a dermatological composition. The composition according to the invention may be formulated in different preparations adapted to topical administration, oral administration or rectal administration, or to parenteral administration. Preferably, the different preparations are adapted to topical administration and include creams, pomades, lotions, oils, patches, sprays and any other products for external application. Administration modes, posologies and optimum galenic forms of the compounds and compositions according to the invention may be determined according to criteria usually used in preparation of a cosmetic or pharmaceutical treatment, preferably dermatological, adapted to a patient such as for example the age or body weight of the patient, the severity of his general condition, his tolerance to treatment, observed side effects, the skin type. Depending on the required administration type, the composition and/or active compounds according to the invention may also comprise at least one cosmetically acceptable or pharmaceutically acceptable excipient, and particularly a dermatologically acceptable excipient. Preferably, an excipient adapted for administration by external topical method will be chosen. The composition according to this invention may also comprise at least one additive cosmetically or pharmaceutically known to those skilled in the art, chosen from among thickeners, preservation agents, perfumes, colouring agents, chemical or mineral filters, moisturising agents, mineral water, etc.

This invention also relates to the compositions described above for their use as medicine.

This invention also relates to the use of at least one active compound chosen from among the alkanolamides group as defined above or a composition according to the invention for the preparation of a medicine designed to inhibit migration of dendritic cells, dermal dendrocytes, monocytes, lymphocytes, keratinocytes, mastocytes and endothelial cells.

According to one particular embodiment of the invention, the medicine is intended to inhibit migration of Langerhans cells.

Advantageously, the said medicine is intended for the treatment or prevention of allergic and/or inflammatory and/or irritative reactions or pathologies of the skin and/or mucosa, particularly of the mouth, the lungs, bladder, rectum and vagina.

Advantageously according to this invention, the medicine is intended for the treatment and/or prevention of reactions or pathologies of the skin and/or mucosa following migration of cells such as Langerhans cells, induced by a danger signal. For the purposes of this invention, a "danger signal" means any signal that in particular leads to the production of inflammatory cytokines or any true immunologic signal such as penetration of an allergen.

According to one embodiment of this invention, the medicine is intended for the treatment and/or prevention of reactions or pathologies induced by chemical or metallic haptens.

According to another embodiment of this invention, the medicine is intended for the treatment or prevention of sensitive and/or reactive and/or uncomfortable and/or intolerant skin and/or mucosa, and/or skin and/or mucosa exhibiting a barrier disorder and/or exhibiting an immunologic imbalance related to intrinsic aging, extrinsic aging (sun, pollution) or hormonal aging.

It has been shown that aging of the skin causes a modification to the immunity status of the skin and that the initial location of immunologic cells can be modified as a result of uncontrolled migration.

The composition according to the invention, and the active compounds according to the invention, can reduce the immunity response induced by migration of LCs that had fixed IgE on the surface. This is why this invention also relates to the use of a composition according to the invention and intended to inhibit the migration of Langerhans cells or at least one active compound chosen from among the oxazolines group as described above for the treatment or prevention of atopic eczema. The composition according to the invention and active compounds according to the invention, are also intended for the treatment or prevention of complex eczema, provided that they can reduce an immunoresponse induced particularly by capture of an antigen, treatment and presentation of this antigen by LCs to T lymphocytes.

The composition according to the invention, and active compounds according to the invention, are also used for the treatment and/or the prevention of inflammatory pathologies, particularly inflammatory dermatitis such as psoriasis, irritative dermatitis, auto-immune diseases, prevention of photo-immuno-suppression or graft rejection. "Photo-immuno-suppression" for the purposes of this invention means a reduction of the immuno response induced by solar ultra-violet rays and particularly by B ultra-violet rays.

The composition according to the invention, and active compounds according to the invention, are also used to reduce the allergising and/or irritant nature of a composition that may be a pharmaceutical preparation or a cosmetic preparation or a perfume. The term "allergenic nature" means the capacity of some compounds contained in the said preparation to behave like allergens, in other words compounds capable of inducing an immediate and/or an inflammatory hyper-sensitivity reaction.

In the various uses mentioned above of the active compound chosen from the alkanolamides group as defined above, the active compound may be used in association with at least one Langerhans cell migration inhibitor selected from among the group composed of matrix metalloprotease (MMP) inhibitors, PKC inhibitors, anti-inflammatory agents, soothing agents, immunosuppressors, ion chelating agents, oxazolidinones, derivatives of carbamic acid and oxazolines as defined above.

The composition and active compounds according to the invention are advantageously intended for use in cosmetology. This invention also relates to a method of cosmetic treatment of the skin and/or mucosa selected from among sensitive, irritated, intolerant skin and/or mucosa, or allergy-prone skin and/or mucosa, or aging skin and/or mucosa or to which a danger signal is applied, exhibiting a barrier disorder, with skin rashes, or exhibiting a non-pathological immunologic imbalance related to intrinsic aging, extrinsic aging or hormonal aging, characterised in that it consists of applying a cosmetic composition according to the invention or at least one active compound chosen from among the alkanolamides group as defined above, onto the skin and/or mucosa. The active compound chosen in the alkanolamides group as defined above may also be applied in association with at least one other compound selected from the group composed of matrix metalloprotease (MMP) inhibitors, PKC inhibitors, anti-inflammatory agents, soothing agents, immunosuppressors, ion chelating agents, oxazolidinones, carbamic acid derivatives and oxazolines as defined previously. Within the context of the cosmetic treatment method according to this invention, the non-pathological immunologic imbalance is a temporary or permanent imbalance of the skin immunity function without being severe.

Other characteristics and advantages of the invention are given in the remainder of the disclosure with the examples given below. These examples refer to the figures given below. These figures and examples are intended to illustrate this invention and may in no case be interpreted as being capable of limiting its scope.

FIGURES

FIG. 1: migration index of Langerhans cells freshly isolated from human skin and activated by DNSB. Effect of the alkanolamide molecule AK100 on the migrational phenomenon. (1) control cells; (2) cells sensitised by DNSB hapten; (3) cells sensitised by DNSB hapten+AK100 (1 µM).

Figure 2:
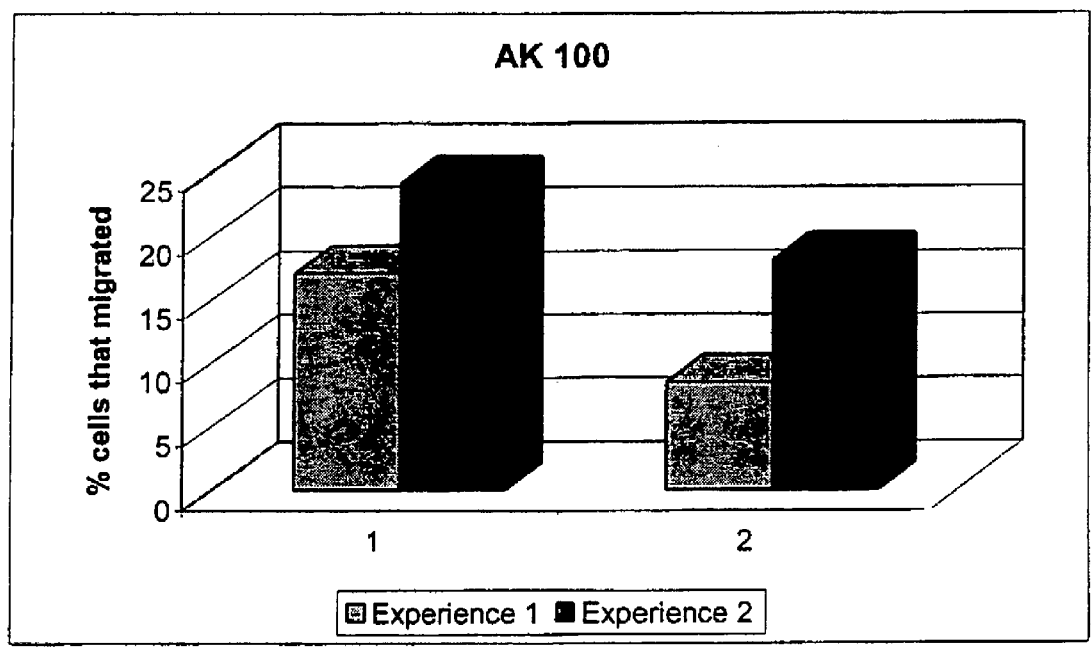

FIG. 2: Percent (%) of migration of dendritic cells derived from blood from the umbilical cord, after activation by hapten. Effect of the alkanolamide molecule AK100 on the migrational phenomenon. (1) cells sensitised by hapten BB; (2) cells sensitised by BB hapten+AK100 (1 µM).

EXAMPLES

Example 1

Example Composition According to this Invention

|  | % by weight |
|---|---|
| Water | QSP 100 |
| Hydrogenated polydecene | 5 to 8 |
| Glycerine | 4 to 17 |
| Dicaprylyl carbonate | 4 to 9 |
| Lauryl glucoside | 1 to 4.5 |
| Polyglyceryl-2 dipolyhydroystereate | 2 to 5 |
| Peptide extract of lupin (hydrolysed protein) | 0.1 to 3 |
| Acrylate/Copolymer alkyl acrylate in $C_{10\text{-}30}$ | 0.4 |
| Sodium hydroxymethylglycinate | 0.4 |
| Xanthane gum | 0.3 |
| Alkanolamide AK100 | 0.01 to 0.8 |
| Sodium hydroxide | 0.07 |
| Citric acid | 0.03 |

Example 2

Study of the Activity of AK100 on Inhibition of Migration of LCs Freshly Isolated from Fragments of Human Skin Equipment and Methods Obtaining Langerhans cells Epidermal cell suspensions were obtained by enzymatic treatment (0.05% trypsine for 18 h at +4° C.) of fragments of normal human skin taken from plastic surgery. The suspensions obtained contain an average of 2 to 4% of LC. Obtaining suspensions containing an average of 70% of LC is based on the principle of centrifuging on density gradient (Lymphoprep™) and elimination of keratinocytes.

Preparation of Media

The basic medium chosen for the entire study was PRMI 1640 (Gibco BRL, France). The AK100 molecule supplied by Pharmascience, with a concentration of $10^{-2}$ M in solution in DMSO (Dimethyl Sulfoxide) was diluted in RPMI-1640 and tested at 1 µM.

Sensitisation of LCs

The sensitising agent was DNSB (Sigma Aldrich), a soluble form of DNCB (dinitro-chloro-benzene) solubilised in RPMI-BSA and used at a concentration of 50 µM.

Migration of LCs

A culture chamber system with two compartments (Falcon, Becton Dickinson, France) was used. The upper compartment is separated from the lower compartment by a membrane with 8 µm porosity, on which 50 µg/cm² Matrigel was deposited. The membrane was then covered by proteins forming a film equivalent to a base membrane (laminine, IV collagen, nidogen, entactin, heparane sulfate proteoglycanes). The cells included in the RPMI-BSA medium alone or in the presence of different products are deposited in the upper compartment. The supernatant culture of normal human fibroblasts is added in the lower compartment. After 18 h incubation at 37° C., the number of living cells that passed through the Matrigel and that are located in the lower compartment is counted under a microscope (the LCs are easily identifiable by their dendritic form). Each test is carried out in triplicate.

Results

Table 2 below shows the results illustrated by the histogram in FIG. 1.

TABLE 2

| | LC migration index | | |
|---|---|---|---|
| | 1 | 2 | 3 |
| Migration index | 1 | 2.55 | 1.11 |

Legend for table 2 and histogram in FIG. 1:
1: Control cells
2: Cells sensitised by DNSB hapten
3: DNSB + AK100 (1 µM).

Legend for table 2 and histogram in FIG. 1:

1: Control cells

2: Cells sensitised by DNSB hapten

3: DNSB+AK100 (1 µM).

Migration of LCs

The results represent the ratio between the number of cells that migrated in the presence of DNSB±AK100 and the number of cells that migrated under normal conditions (unsensitised and untreated control cells). LCs freshly isolated from the epidermis do not have a high migration capacity. In the expression of the results, the migrational capacity of control LCs (not treated and not sensitised) is arbitrarily set equal to 1.

The treatment with cells with DNSB hapten stimulated migration of LCs significantly (+155%) compared with normal unstimulated cells (control cells).

AK100 at a concentration of 1 µM significantly inhibits migration of LCs induced by DNSB. The cells thus treated have a migration index comparable to the migration index of unsensitised control cells.

The inventors have demonstrated that, quite surprisingly, AK100 significantly inhibits migration of LCs when freshly isolated LCs are used placed in a culture chamber system with two compartments (enabling cellular migration). Under the experimental conditions used by the inventors, cells treated by AK100 have a migration index comparable to that of unsensitised control cells.

Example 3

Study of the AK100 Activity on Inhibition of Migration of Dendritic Cells Generated in Vitro from CD34+ Precursors Derived from Blood from the Umbilical Cord Equipment and Methods In Vitro Langerhans-Like Generation Mononucleated cells were obtained from blood from the umbilical cord of healthy donors by centrifuging on Ficoll. The CD34+ cells were then purified by immunoselection using a specific antibody and magnetic balls (Miltenyi Biotech, Germany). The CD34+ cells were cultivated in the presence of GM-CSF (100 ng/ml), TNF-α (2.5 ng/ml) in RPMI to which 10% calf foetus serum was added for 5 days. TGF-β1, a factor that encourages differentiation of cells to the Langerhans cells method, was added on the 5$^{th}$ day of culture.

Preparation of media

Ditto example 2.

Sensitisation of LCs

Cells were treated by hapten BB on the 7$^{th}$ day (Brandowski base, 1.17 µg/ml) for 24 h, and were then subjected to the migration test.

Migration of LCs

Ditto example 2.

Results

The results of two independent experiments are given in table 3 below and are illustrated by the histogram in FIG. 2.

TABLE 3

| Percentage of dendritic cells generated in vitro that migrated | | |
|---|---|---|
| | 1 | 2 |
| Experiment 1 | 17 | 8.4 |
| Experiment 2 | 24 | 18 |

Legend for table 3 and histogram in FIG. 2:
1: Cells sensitised by hapten BB
2: BB + AK100 (1 µM).

Migration of LCs

The results represent the percentage of cells that migrated in the presence of the different tested products. The percentage is calculated by taking the ratio of the number of cells recovered in the lower compartment of the migration chamber, to the number of cells subjected to migration. AK100 inhibits the migration of dendritic cells by 51 and 25% in experiments 1 and 2 respectively.

At a concentration of 1 µM, the AK100 significantly inhibits migration of dendritic cells generated in vitro and activated by hapten BB.

Example 4

Study of the Activity of Alkanolamide AK100, Alone or in Association with LU105, on Inhibition of Migration of Dendritic Cells on the Mouse Equipment and Methods Reagents FITC (Fluoresceine isothiocyanate, Sigma, St Louis, Mo.) was extemporaneously diluted in an acetone mix (dibutylphthalate (1:1)).

Inhibitors

Alkanolamide AK100 and LU105 (LU 105 is an MMP inhibitor, corresponding to a peptide extract of white lupin marketed by the Expanscience Company under the brand name Actimp (193®) were supplied by "Laboratoires Expanscience" and formulated alone or association with each other in an inert vehicle compatible with a topical application (alkanolamide AK100 (0.1%)± LU105 (2%)). The different formulations were applied on the ears of mice twice per day for 4 consecutive days. 1.5% of FITC was applied on both ears (one treated and the other not treated (Control)) three hours after the last application.

Migration of Langerhans cells (LC) and dendritic cells (DC) on the mouse.

The effect of the two molecules was evaluated in vivo in the mouse. 1.5% FITC (2×5 µl) was applied on the skin of both ears. 24 h later, the mice were sacrificed and a cellular suspension was prepared from auricular and cervical ganglions (draining ganglions, hereinafter denoted GL) or from the poplital ganglions (non-draining ganglions, negative control). The tissues were cut and cells separated by filtration (100 µm filter, Falcon; Becton Dickinson) and then washed. The cells were then centrifuged for 10 minutes at 600×g (m×s$^{-2}$) on a metrizamide gradient (14.5% in RPMI 1640; 7.5% SVF) The interface cells were retrieved, rinsed and then marked with an anti-CDS86 PE-conjugated, biot-MHC CLII mAbs AC plus streptavidine-Cya (PharMingen) and analysed by flux cytometry. Only the FITC$^+$, PE$^+$ and Cya$^+$ cells are counted since they represent the population of cells that migrated from the skin to GLs following the application of hapten.

Results

Topical application of the vehicle alone did not cause any modification to the number of FITC+ DCs in LGs. Therefore the vehicle does not have any effect on the migratory capacities of DCs.

Table 4 below shows the results for migration of DCs.

TABLE 4

| | ALKANOLAMIDE AK100 (0.1%) | LU105 (2%) | ALKANOLAMIDE AK100 (0.1%) + LU105 (2%) |
|---|---|---|---|
| Migration inhibition in % | 30 | 40 | 90 |

Migration of DCs at LGs after FITC hapten was applied, is inhibited in similar proportions by a 0.1% content of alkanolamide AK100 and a 2% content of LU105, there being no significant difference.

When the two types of molecules are associated, this inhibition is almost complete. In conclusion, it has been quite surprisingly demonstrated that if a model for mice sensitised by FITC hapten is used, alkanolamide AK100 significantly inhibits migration of DCs to LGs. Furthermore, alkanolamide AK100 and Lu105 act in synergy to inhibit the migration of DCs in the sensitised mouse.

Example 5

Study of the Activity of Oxazoline OX100 Alone or in Association with OK100, on Inhibition of the Migration of Dendritic Cells on the Mouse Equipment and Methods
Reagents
FITC (Fluoresceine isothiocyanate, Sigma, St. Louis, Mo.) was diluted extemporaneously in a mixture of acetone and dibutylphthalate (1:1).

Inhibitors

Alkanolamide AK100 and OX100 (described above) were supplied by "Laboratoires Expanscience" and formulated alone or in association in an inert vehicle compatible with a topical application [AK100 (0.05%)±OX100 (0.05%)]. The different formulations were applied on the ears of mice twice per day for 4 consecutive days. Three hours after the last application, 1.5% of FITC was applied on both ears (one treated and the other not treated (Control)).

Migration of Langerhans cells (LC) and dendritic cells (DC) on the mouse.

The effect of the two molecules was evaluated in vivo in the mouse. 1.5% FITC (2×5 µl) was applied on the skin of both ears. 24 h later, the mice were sacrificed and a cellular suspension was prepared from auricular and cervical ganglions (draining ganglions, hereinafter denoted GL) or from the poplital ganglions (non-draining ganglions, negative control). The tissues were cut and cells separated by filtration (100 µm filter, Falcon; Becton Dickinson) and then washed. The cells were then centrifuged for 10 minutes at 600×g (m×s$^{-2}$) on a metrizamide gradient (14.5% in RPMI 1640; 7.5% SVF). The interface cells were retrieved, rinsed and then marked with an anti-CDS86 PE-conjugated, biot-MHC CLII mAbs AC plus streptavidine-Cya (PharMingen) and analysed by flux cytometry. Only the FITC$^+$, PE$^+$ and Cya$^+$ cells are counted since they represent the population of cells that migrated from the skin to GLs following the application of hapten.

Results

Topical application of the vehicle alone did not cause any modification to the number of FITC+ DCs in LGs. Therefore the vehicle does not have any effect on the migratory capacities of DCs.

Table 5 below shows the results for migration of DCs.

TABLE 5

| | AK100 (0.05%) | OX100 (0.05%) | AK100 (0.05%) + OX100 (0.05%) |
|---|---|---|---|
| Migration inhibition in % | 15 | 15 | 40 |

Migration of DCs at LGs after FITC hapten was applied, is inhibited in similar proportions by a 0.05% content of AK100 and a 0.05% content of OX100, there being no significant difference.

When the two types of molecules are associated, this inhibition is greater. In conclusion, it has been quite surprisingly demonstrated that if a model of mice sensitised by FITC hapten is used, alkanolamide AK100 significantly inhibits migration of DCs to LGs. Furthermore, alkanolamide AK100 and OX100 act in synergy to inhibit the migration of DCs in the sensitised mouse.

Example 6

Evaluation of the Effects of a Cosmetic Day Cream Comprising Alkanolamide AK100 for a Hypersensitive, Irritated Skin or Allergy-Prone Skin A cosmetic day cream comprising 0.1% by weight of AK100 and 2% by weight of peptide extract from white lupin, LU105, as a function of the total weight of the cream, was tested on human volunteers, with the cooperation of dermatologists.

The main purposes were to evaluate the clinical efficiency and cosmetic acceptability of the said day cream in the context of normal use of the product.

The test product was provided to the practitioner with the necessary public information, and the Dermatologist proposed it to his patient specifying sufficient daily application methods, namely at least 2 applications per day. The product was applied to the face morning and evening on a clean and dry skin.

The total duration of the study for each volunteer was 4 weeks with two observations, recorded before and then after this 4-week application period.

The volunteer was non-directively questioned about the possible occurrence of undesirable local effects during the final visit.

The tests were carried out in accordance with the protocol described above on 37 women.

The results were evaluated on a scale varying from 0 to 9. A mark of 0 corresponds to zero change of the skin before and after the treatment, a mark varying from 1 to 3 corresponds to a slight change of the skin before and after the treatment, a mark from 4 to 6 corresponds to a moderate change to the skin before and after the treatment, and a mark from 7 to 9 corresponds to a large change to the skin before and after the treatment.

Tables 6 to 8 below contain the results.

TABLE 6

Dermatological clinic evaluation on women with sensitive and/or irritated skin:

| | Erythema | Dryness | Desquamation | Oedema | Vesicles | Roughness | Pruritus | Smarting | Burning Sensation | Pain |
|---|---|---|---|---|---|---|---|---|---|---|
| Average mark out of 10 on D0 | 4.24 | 4.84 | 2.95 | 0.70 | 0.16 | 1.68 | 3.16 | 2.95 | 3.49 | 0.89 |
| Average mark out of 10 on D30 | 1.68 | 1.68 | 0.89 | 0.08 | 0.00 | 0.32 | 0.70 | 0.57 | 0.43 | 0.11 |
| % change from D0 to D30 | −61% | −65% | −70% | −88% | −100% | −81% | −78% | −81% | −88% | −88% |

TABLE 7

Dermatological clinic evaluation on women with sensitive skin:

| | Erythema | Dryness | Desquamation | Oedema | Vesicles | Roughness | Pruritus | Smarting | Burning sensation | Pain |
|---|---|---|---|---|---|---|---|---|---|---|
| Average mark out of 10 on D0 | 3.90 | 5.00 | 2.35 | 0.55 | 0.25 | 1.60 | 2.70 | 3.35 | 4.15 | 0.55 |
| Average mark out of 10 on D30 | 1.75 | 1.65 | 0.50 | 0.00 | 0.00 | 0.40 | 0.30 | 0.55 | 0.40 | 0.05 |
| % change from D0 to D30 | −55% | −67% | −79% | −100% | −100% | −75% | −89% | −84% | −90% | −91% |

TABLE 8

Dermatological clinic evaluation on women with irritated skin:

| | Erythema | Dryness | Desquamation | Oedema | Vesicles | Roughness | Pruritus | Smarting | Burning sensation | Pain |
|---|---|---|---|---|---|---|---|---|---|---|
| Average mark out of 10 on D0 | 4.65 | 4.65 | 3.65 | 0.88 | 0.06 | 1.76 | 3.71 | 2.47 | 2.71 | 1.29 |
| Average mark out of 10 on D30 | 1.59 | 1.71 | 1.35 | 0.18 | 0.00 | 0.24 | 1.18 | 0.59 | 0.47 | 0.18 |

TABLE 8-continued

| | Erythema | Dryness | Desquamation | Oedema | Vesicles | Roughness | Pruritus | Smarting | Burning sensation | Pain |
|---|---|---|---|---|---|---|---|---|---|---|
| % change from D0 to D30 | −66% | −63% | −63% | −80% | −100% | −87% | −68% | −76% | −83% | −86% |

These various results show that the said day cream significantly improves the condition of hypersensitised, irritated skin and allergy-prone skin. These data were confirmed by volunteers who were 95% satisfied with the cream that gives an immediate sensation of comfort (100%), attenuates reactions to aggression by pollution and the climate (62%), calms irritation (88%), protects and soothes (80%), and increases the tolerance threshold (76%).

Thus the said cream, formulated without perfume or colouring agent, efficiently moisturises the upper layers of the epidermis and provides an appropriate response to hypersensitive, irritated and allergy-prone skin.

In conclusion, it has thus been demonstrated quite surprisingly, that AK100 in association with LU105 inhibits almost all migration of DCs to LGs. Moreover, AK100 and LU105 act in synergy to inhibit migration of DCs in a sensitised mouse.

It has thus quite surprisingly been demonstrated that the same proportions of AK100 and LU105 incorporated into a cosmetic cream enable effective moisturisation of the upper layers of the epidermis and provide an appropriate solution to hyper sensitive, irritated or allergy-prone skin.

The invention claimed is:

1. A method for treating conditions or disorders which comprises:

inhibiting migration of dentritic cells, dermal dendrocytes, monocytes, lymphocytes, keratinocytes, mastocytes and endothelial cells in a living animal body exposed to an agent that induces the cutaneous immune response, by administering to the living animal body an effective amount of a composition comprising AK100 at a concentration between 0.01 and 3% by weight, said AK100 having the following formula:

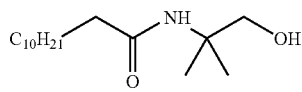

and peptide extracts of lupin at a concentration between 0.1 to 3% by weight, wherein the conditions or disorders are selected from an allergic, an inflammatory, or an irritative reaction or pathology of the skin or mucosa due to a migration of Langerhans cells, a reaction or a pathology induced by chemical or metallic haptens, sensitive skin, atopic eczema, contact eczema, inflammatory dermatitis, irritative dermatitis, auto-immune diseases, or graft rejection.

2. The method of claim 1, wherein the migration of Langerhans cells in inhibited.

3. The method as claimed in claim 1, wherein the inflammatory dermatitis is psoriasis.

4. The method of claim 1, wherein the composition further comprises a compound chosen from the group constituted by PKC inhibitors, anti-inflammatory agents, soothing agents, immunosuppressors, ion chelating agents, oxazolines, oxazolidinones and derivatives of carbamic acid.

5. The method according to claim 1, wherein the AK100 is at a concentration of 0.1% weight and the peptide extracts of lupin is at a concentration of 2% by weight.

6. The method according to claim 1, wherein the cutaneous immune response induced by the agent comprises the migration of Langerhans cells followed by capture of a surface antigen, and wherein the Langerhans cells present the antigen to T cells.

7. The method according to claim 1, wherein the agent is an antigen.

8. The method according to claim 1, wherein the agent is an allergen.

9. The method according to claim 1, wherein the composition further comprises retinoids.

* * * * *